United States Patent
Villar et al.

(10) Patent No.: US 6,287,318 B1
(45) Date of Patent: Sep. 11, 2001

(54) VASO-OCCLUSIVE DEVICE WITH ATTACHED POLYMERIC MATERIALS

(75) Inventors: Francisco S. Villar, Newark; Nestor Aganon, San Jose, both of CA (US)

(73) Assignee: Target Therapeutics, Inc., Fremont, CA (US)

( * ) Notice: Subject to any disclaimer, the term of this patent is extended or adjusted under 35 U.S.C. 154(b) by 0 days.

(21) Appl. No.: 09/318,018

(22) Filed: May 25, 1999

Related U.S. Application Data

(63) Continuation of application No. 09/023,564, filed on Feb. 13, 1998, now Pat. No. 5,935,145.

(51) Int. Cl.⁷ .................................................. A61M 29/00
(52) U.S. Cl. .................................................. 606/191
(58) Field of Search ........................ 606/191, 1, 104, 606/170, 32; 424/422, 423, 426

(56) References Cited

U.S. PATENT DOCUMENTS

| | | |
|---|---|---|
| 4,739,768 | 4/1988 | Engelson . |
| 4,994,069 | 2/1991 | Ritchart et al. . |
| 5,122,136 | 6/1992 | Guglielmi . |
| 5,226,911 | 7/1993 | Chee et al. . |
| 5,250,071 | 10/1993 | Palermo et al. . |
| 5,382,259 | 1/1995 | Phelps et al. . |
| 5,490,859 | 2/1996 | Mische et al. . |
| 5,522,836 | 6/1996 | Palermo . |
| 5,549,624 | 8/1996 | Mirigian et al. . |
| 5,700,258 * | 12/1997 | Mirigian et al. ............... 606/1 |
| 5,733,294 | 3/1998 | Forber et al. . |
| 5,743,905 | 4/1998 | Eder et al. . |
| 5,800,454 | 9/1998 | Jacobsen et al. . |
| 5,823,198 * | 10/1998 | Jones et al. ................. 606/1 |
| 5,855,578 | 1/1999 | Gugliemi et al. . |
| 5,891,128 | 4/1999 | Gia et al. . |
| 5,891,130 | 4/1999 | Palermo et al. . |
| 5,895,385 | 4/1999 | Gugliemi et al. . |
| 5,895,391 | 4/1999 | Farnholtz . |
| 5,911,717 | 6/1999 | Jacobsen et al. . |
| 5,916,235 | 6/1999 | Gugliemi . |
| 5,919,187 | 7/1999 | Guglielmi et al. . |
| 5,925,037 | 7/1999 | Fober . |
| 5,925,060 | 7/1999 | Forber . |
| 5,925,062 | 7/1999 | Purdy . |
| 5,927,345 | 7/1999 | Samson . |
| 5,928,226 | 7/1999 | Gugliemi et al. . |
| 5,944,714 | 8/1999 | Gugliemi et al. . |

FOREIGN PATENT DOCUMENTS

| | | | |
|---|---|---|---|
| 0778005 * | 6/1997 | (EP) | ............ 606/1 |
| WO 94/09705 | 5/1994 | (WO) . | |
| 94/10936 * | 5/1994 | (WO) | ............ 606/1 |
| 94/15534 * | 7/1994 | (WO) | ............ 606/1 |
| WO 95/20916 | 8/1995 | (WO) . | |
| WO 96/00035 | 1/1996 | (WO) . | |
| WO 97/48351 | 12/1997 | (WO) . | |
| WO 98/02100 | 2/1998 | (WO) . | |
| WO 98/04198 | 2/1998 | (WO) . | |
| WO 98/04315 | 2/1998 | (WO) . | |

* cited by examiner

Primary Examiner—David O. Recla
Assistant Examiner—(Jackie) Tan-Uyen T. Ho
(74) Attorney, Agent, or Firm—Morrison & Foerster LLP

(57) ABSTRACT

A device for occluding a space within the body, and particularly,the device usefle as a vaso-occlusive device. In partiular, the device typically comprises a metallic core or core member, and two polymeric conjuncts, often polymeric members, of differing thrombogenicity. Typically, the core member comprises a metallic helically-wound coil; the first polymeric member and second polymeric member are fibrous materials woven into a braid. The device may be placed at the desired site within a mammal to facilitate the formation of an occlusion. The device promotes the formation of scar tissue, healing tissue, or neocapillaries in vascular occlusions made by the device.

16 Claims, 4 Drawing Sheets

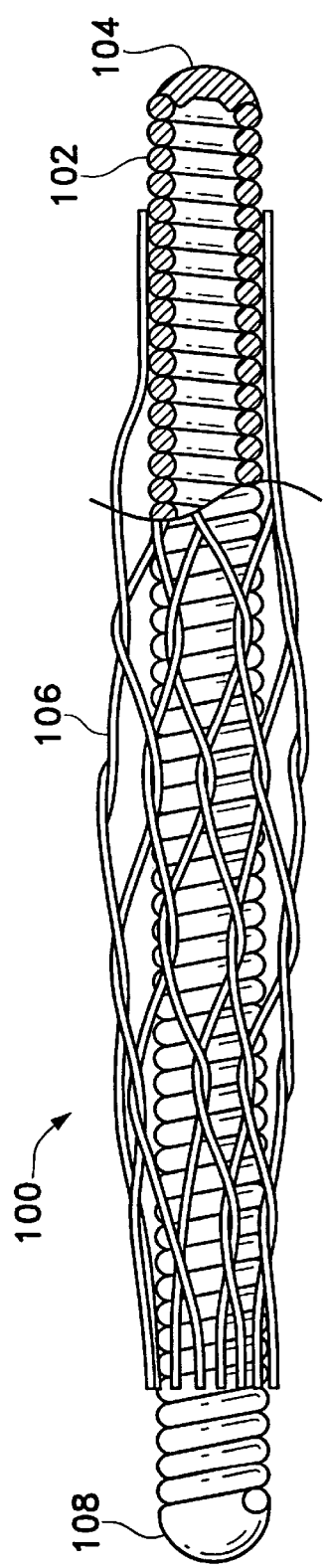
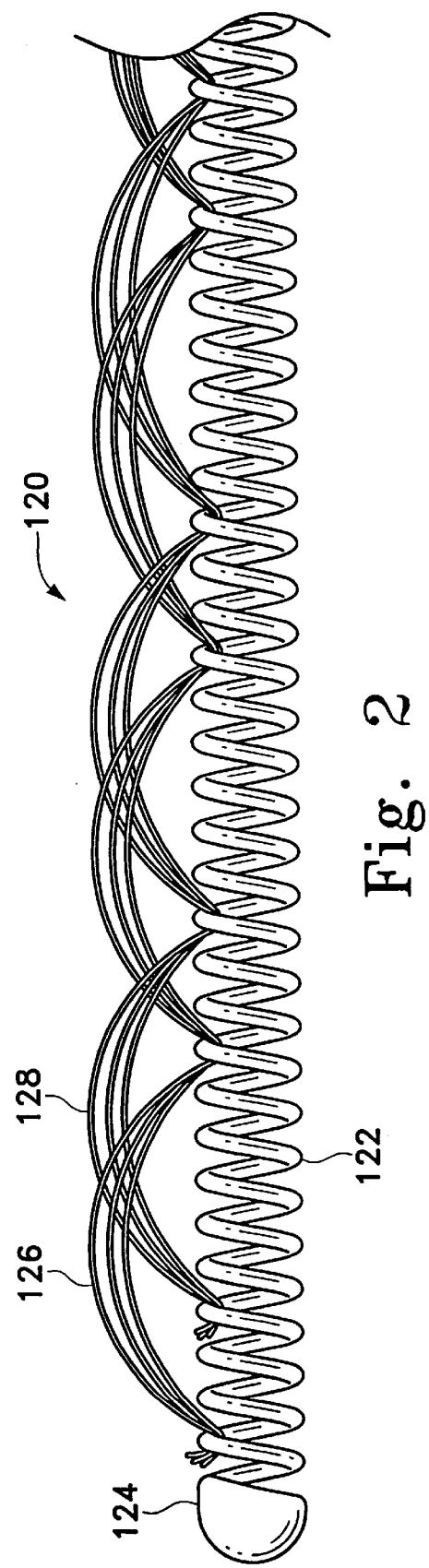

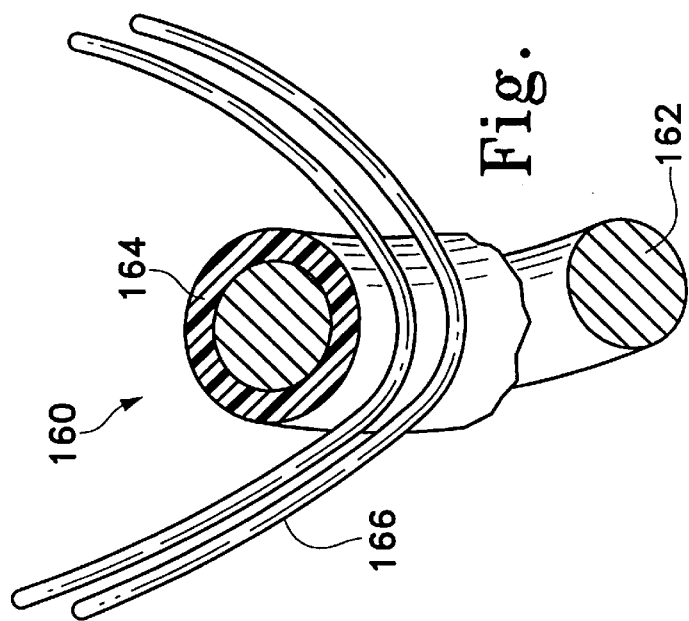
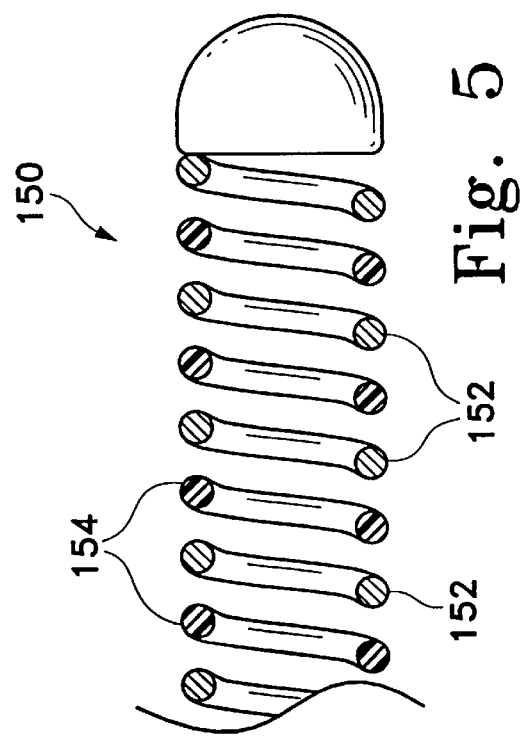
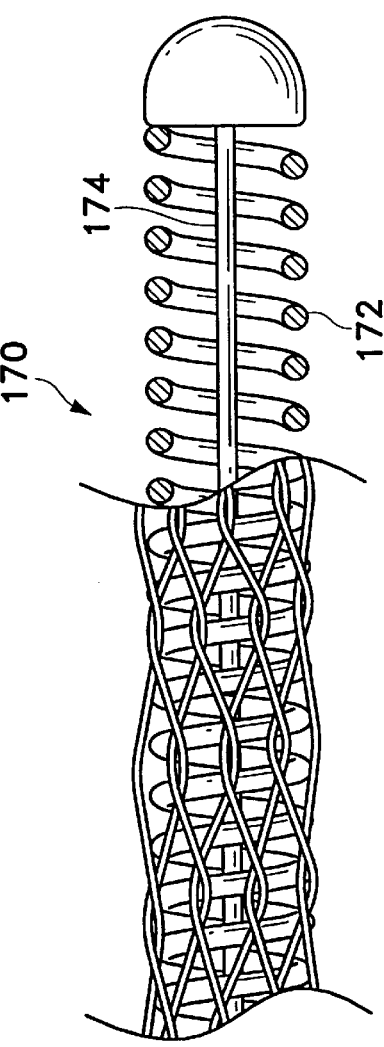

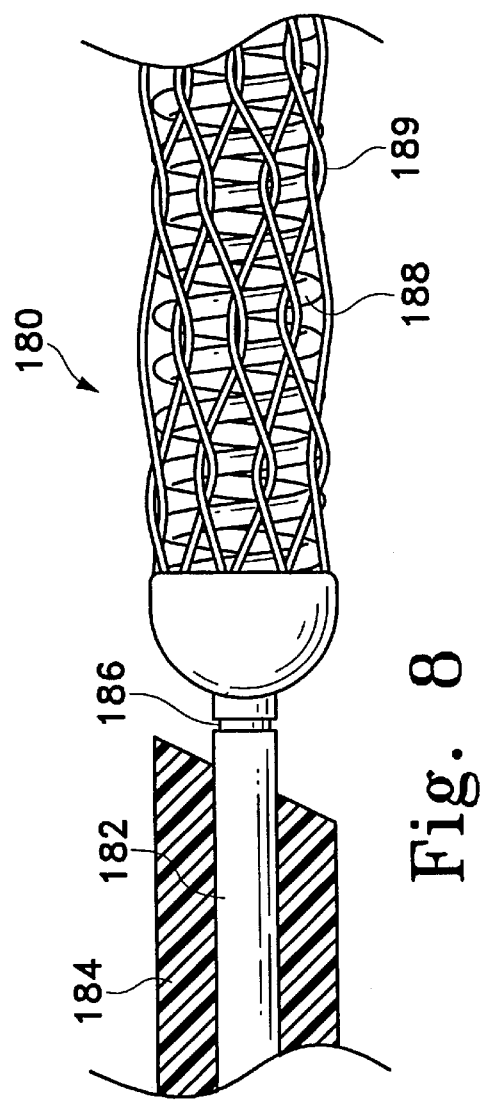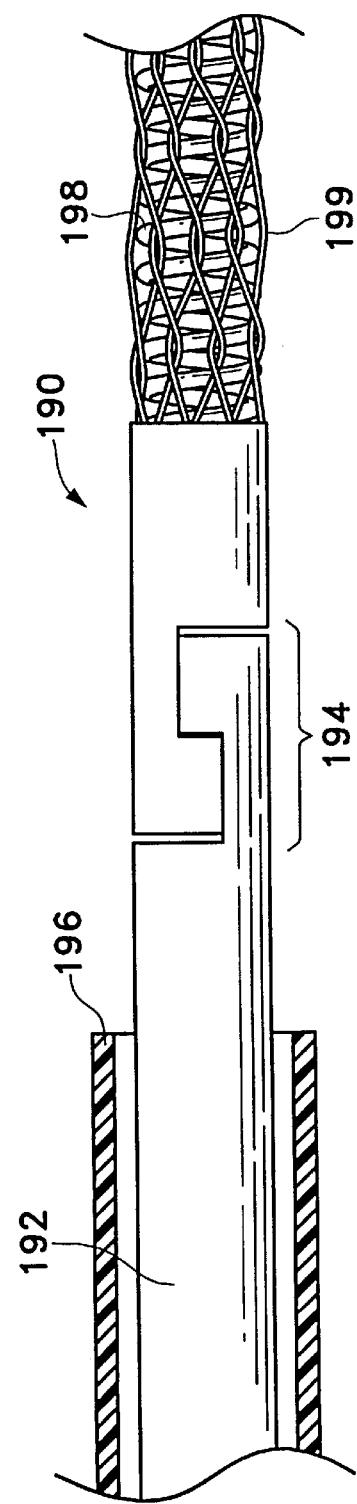

VASO-OCCLUSIVE DEVICE WITH ATTACHED POLYMERIC MATERIALS

This application is a continuation of U.S. Pat. application Ser. No. 09/023,564, entitled "VASO-OCCLUSIVE DEVICE WITH ATTACHED POLYMERIC MATERIALS", filed Feb. 13, 1998, now U.S. Pat. No. 5,935,145.

FIELD OF THE INVENTION

This invention relates to a device for occluding a space within the body, and particularly, it is useful as a vaso-occlusive device. In particular, it typically comprises a metallic core or core member, and two polymeric conjuncts, often polymeric members, of differing thrombogenicity. Typically, the core member will comprise a metallic helically-wound coil and the first polymeric member and second polymeric member will be fibrous materials woven into a braid. These devices may be placed at the desired site within a mammal to facilitate the formation of an occlusion. The inventive device has been found to promote the formation of scar tissue, healing tissue, or neocapillaries in vascular occlusions made by the device.

BACKGROUND OF THE INVENTION

Occlusive devices used for the blocking of openings within the human body, particularly vaso-occlusive devices, are now well-known and widely accepted as specific treatments for a variety of maladies. Although we often discuss the invention herein as one dealing with the occlusion of blood vessel or aneurysm closure, the invention is not so limited and may be used in a variety of other sites in the human body, e.g., fallopian tubes, bile ducts, etc. All members of the class of vaso-occlusive devices are surgical implements that may be placed within the vasculature of the human body, typically by a catheter, either to block the flow of blood through the vessel making up that portion of the vasculature, or to fill an aneurysm which stems from such a vessel. One member of the class of widely used vaso-occlusive devices includes the helically wound wire coil. Fibers may be woven into or laid crosswise through the coil windings to provide an additional substrate for clot formation and tissue growth within the chosen site. Vaso-occlusive devices having such a structure are widely commercially available from, for instance, Target Therapeutics Inc.

One very early patent, U.S. Pat. No. 4,994,069, to Ritchart et al., describes such a vaso-occlusive coil. This vaso-occlusive device assumes a linear helical configuration when placed within a delivery catheter and a folded, convoluted configuration when relaxed after having been released from the delivery catheter. Ritchart et al. describes a number of secondary or relaxed configurations, each of which is suitable for a specific type of malady.

U.S. Pat. No. 5,226,911, to Chee et al., teaches a helical vaso-occlusive coil to which fibrous elements are attached in such a way that they will not be dislodged during use. The fibrous elements are placed on the coil to enhance the tendency of the coil assembly to cause clot formation and tissue growth.

U.S. Pat. No. 5,382,259, to Phelps et al., teaches a vaso-occlusive device having a braided covering produced of polymeric fibrous elements on the exterior of the device. A variety of biocompatible materials are shown as suitable for the braided exterior tubular member.

Although these patents and others describe vaso-occlusive devices having metallic substrates and fibrous additions, none of them show the combination of polymeric materials as described here nor their utility in promoting tissue growth. Specifically, none of the references discussed above suggest that the noted combination is able to produce neocapillary formation in the vasculature.

SUMMARY OF THE INVENTION

This invention is an occlusive device suitable for placement in an internal area of the human body. It may be, and preferably is, used in the vasculature either in the open lumen of an artery or vein, in a somewhat more quiescent area such as the interior of an aneurysm, or perhaps to close a fistula or similar structure such as an arterio-venous malformation (AVM). When used in the vasculature, the occlusive device of this invention has been found to facilitate the formation of neocapillaries, scar tissue, cellular growth, or healing tissue in the occlusion.

The device itself typically comprises three components. The first is a core element and typically is a helically-wound coil. Braids or multiple coils or their combinations are also suitable as the core element. The remaining two components are polymeric in nature. The first is a polymer, typically in a fibrous form, which is present in the inventive device quickly to form clots when placed in the vasculature.

The second polymeric component typically composed of a polymer which is degradable or dissolvable within the human body. Especially preferred is polyglycolic acid.

It is within the scope of this invention that the polymeric components are either separate, e.g., in filamentary or covering form, or in the form of a mixture or copolymer (block or random) of the two polymeric components.

The preferred structure comprises a helically-wound core member produced of platinum wire (or other biocompatible material). The two polymeric materials are preferably wound into a braid, placed on the exterior of the coil, and fastened (perhaps by gluing or heat shrinking or melting) at the ends of the braid onto the coil. It is not, however, believed that the physical structure of the device is critical but that the combination of a bulk core member and two different types of polymeric materials as outlined above is central to the invention.

BRIEF DESCRIPTION OF THE DRAWINGS

FIG. 1 shows a partial cross-section of the preferred variation of the inventive occlusion device including a coil and a braided covering.

FIG. 2 shows a variation of the inventive device involving a coil and a looping of fibrous members.

FIG. 5 shows a variation in which one of the polymeric members is included as a portion of the core member.

FIG. 6 shows a variation of the inventive device in which one of the polymeric members is partially coated onto the central core member.

FIG. 7 is a partial cross-section of the inventive device and shows the use of a stretch-resisting member.

FIG. 8 shows a partial cross-section of a device made according to the invention in which the device is deliverable using an electrolytically severable joint.

FIG. 9 shows a variation of the inventive device in which the inventive device is deliverable using a mechanically-detachable joint.

DESCRIPTION OF THE INVENTION

Figure 3:
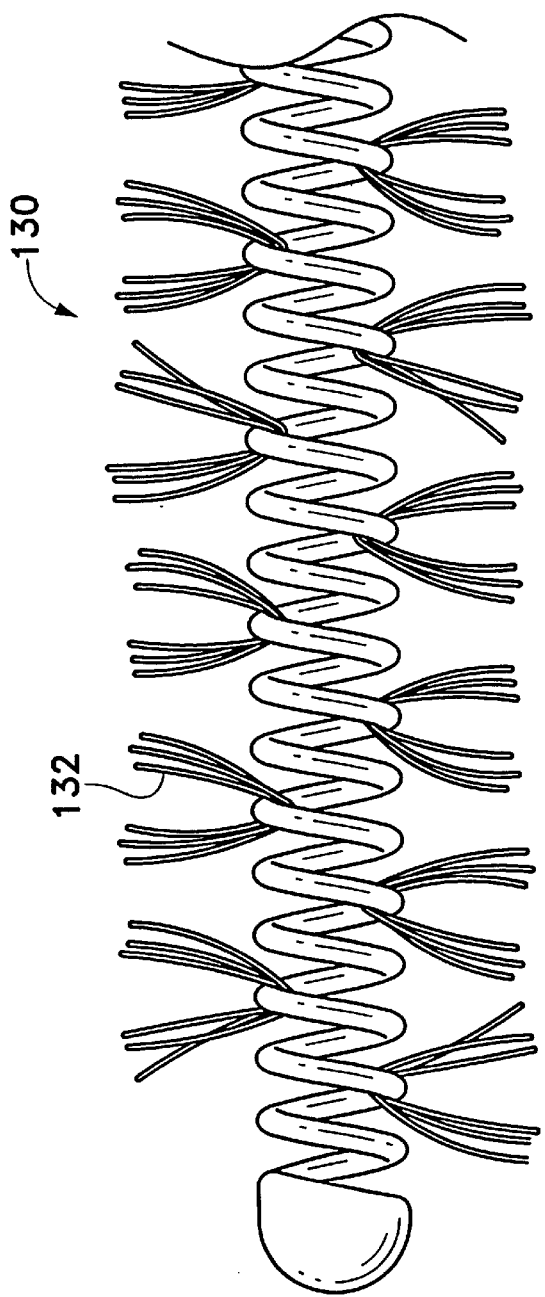
FIG. 3 shows another variation of the device involving a helically-wound coil and tufted fiber members.

The occlusive devices of this invention may be used and delivered in a manner similarly to the procedures described in U.S. Pat. No. 5,382,259, to Phelps and Van, the entirety of which is incorporated by reference. Procedures for using these coils are sufficiently well known that they need be described only in narrative form. Specifically, the devices may be supplied in a pre-packaged form in a sterile cannula, which cannula is able to engage the proximal end of a delivery catheter. Placement of microcatheters to, e.g., an aneurysm within the brain is well-known and documented. Procedures such as found in U.S. Pat. No. 4,739,768, to Engelson (incorporated by reference), are suitable. That is to say that a large guide catheter is first inserted into a femoral artery in the groin region and moved forward through that artery towards the heart. In the region of the heart, it is passed through the aortic arch and into an appropriate artery and then forwarded through the neck region. Into this larger guide catheter is then placed a combination of a microcatheter and a guide wire. The guide wire and microcatheter are forwarded through the guide catheter and, upon reaching the end of the guide catheter, the guide wire is then passed into the brain. As selections of vessels are made, the catheter is slid along the guide wire in a tandem motion. Once the guide wire is introduced into the selected site, e.g., an aneurysm, the distal tip of the catheter is introduced into the aneurysm as well. The guide wire is then removed. Removal of the guide wire provides an open channel between the exterior of the body and the interior of an aneurysm, the aneurysm being perhaps deep within the brain. The vaso-occlusive devices of this invention may then be introduced into the aneurysm by simply pushing them through the interior of the microcatheter after they have been dislodged from their feed cannula. They may also be controllably detached either by using devices such as those shown in U.S. Pat. No. 5,122,136, by Guglielmi el al., or using mechanical detachment joints. Dr. Guglielmi's device involves the use of an electrolytically-severable (or electrical erodible) joint between the pusher wire and the vaso-occlusive device. This variation is discussed in more detail below. Other similar mechanical joints are known and will be discussed below as well.

In any event, once the inventive device has been delivered from the distal end of the delivery catheter, perhaps with multiple delivery of coils, the catheter may then be removed. The inventive device then goes about forming an occlusion. We have found that the combination of polymeric materials described herein facilitates the formation of neocapillary regions in the occlusion. This is an effect we have not seen in the other related vaso-occlusive devices we have studied.

FIG. 1 shows in partial view one highly desirable variation of this invention (100). It is made up of several components. The first component is core member (102). In this variation, core member (102) is a helically-wound coil preferably, although not necessarily, formed from a biocompatible metallic material such as platinum, or more likely, an alloy of platinum and a few percent of tungsten. Core member (102) is preferably, but not necessarily, radio-opaque. Other compatible metals such as gold, rhodium, rheniun, palladium, and other members of the platinum group of metals of the periodic table are also suitable. The core member may also be formed from a polymeric material such as nylon, polyethylene, polypropylene, carbon fiber, collagen, or other synthetic or natural polymeric materials. Most preferred is an alloy of platinum and a few percent of tungsten.

It is desirable in any of the variations described herein that the ends (104 and 106) of helically-wound coil (102) be blunted or otherwise formed as is shown in FIG. 1. One classic way of rendering the ends of the coil is by heating the coil so to melt the material of the coil. Of course, it is quite desirable as well and often easier to form the ends of the coil using the addition of thermoplastic polymer. Suspensions of polymers in carrier solvents may also be used.

The braid (106) shown in FIG. 1 on the exterior of coil (102) is made of two polymeric, fibrous members. The braid (106) in this variation is made up of fibers of first polymeric member which is highly thrombogenic and not typically susceptible to absorption in the human body. The braid (106) is further made up of fibers selected from members of a second group of polymers which are generally considered to be absorbable in the human body. Members of the first polymeric component set include polymers of the group polyethyleneterephthalate (Dacron), polyethylene, polypropylene, most of the Nylons, aramids, and the like.

Members of the second group of polymeric components include those materials which are considered to be absorbable in the human body. Materials which are used to make absorbable sutures are members of this group. Desired members include polyglycolic acid, polylactic acid, cotton, silk, and the like.

The wire making up coil (102) will typically have a diameter in the range of 0.0005 and 0.005 inches. The resulting primary coil diameter will normally be in the range of 0.004 to 0.038 inches. Preferably, the coil primary diameter is 0.015 to 0.018 inches, although coils having diameters down to 0.008 inches and formed from a platinum wire of 0.001 inches diameter are sold by Target Therapeutics for specific treatments. The axial length of a coil made according to this invention will typically be in the range of 0.05 to 100 centimeters, more typically in the range of 2.5 to 40 centimeters. The coil will typically have 10 to 70 windings per centimeter, more typically about 10 to 40 windings per centimeter. The coil windings may have a regular or constant pitch as is shown in FIG. 1 or they may vary in pitch as desired to provide the coil with a variation in flexibility.

The strands forming the braid typically are fibrous elements made up of a bundle of individual fibers, e.g., between 5 and 100 fibers per fibers bundle. The fibrous elements may be monofilament if so desired.

The preferred first polymeric component is polyethyleneterephthalate,e.g., Dacron, and the preferred second polymeric component is polyglycolic acid.

FIG. 2 shows another variation (120) of the inventive occlusion device. In this variation, coil (122) also has a constant diameter although it is somewhat more stretched than is the coil shown in FIG. 1. Coil (122) also has coil ends (124) as was the case with the coil shown in FIG. 1. In this variation, the respective fibrous elements (126 and 128) are looped through the turns of the coil. The materials shown as looping filaments (126 and 128) are shown in this way because they provide the resulting device with a lower overall effective diameter making it easier to deliver through a delivery catheter. The fibrous materials need not be looped in this way. Others are suitable. The fibers from the first and second polymeric member groups listed above may be intimately intermixed or placed apart from each other.

FIG. 3 shows another variation (130) of the inventive device. In this variation, the fibers (132) making up the tufts of the two different groups of materials may be intermixed or segregated as desired.

Figure 4:
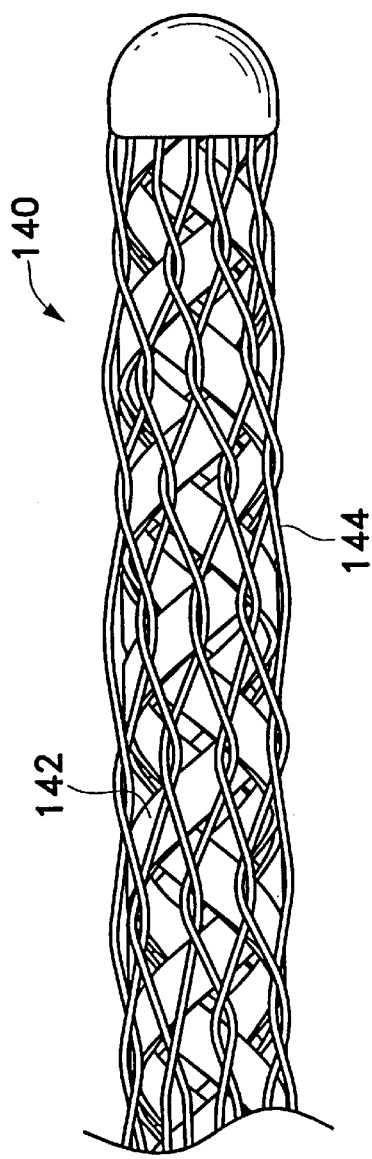
FIG. 4 shows a partial side view of a variation in which the core member is a braided member and the fibrous members are woven as a braid exterior to the core member.

FIG. 4 shows still another variation of the inventive device (140) in which the central core is a braid (142)

composed of ribbon rather than the wire coils discussed above. The ribbon materials are woven in a radial in and out fashion so to form a structure which does not unwind itself. The mechanics of making such a braid are well-known and, for instance, may be found in U.S. Pat. application Ser. No. 08/640,342, filed Apr. 30, 1996, to Samson, the entirety which is incorporated by reference. As was the case with the FIG. 1 variation, the braid structure (142) is within polymeric braid (144). Polymeric braid (144) includes fibrous materials from each of the two classes of polymers discussed above.

FIG. 5 shows a partial cutaway of device (150) in which two coils are interwoven with each other in the same direction on the device (150), the outer fibrous materials allied are omitted for the purpose of clarity in this figure. In any event, variation (150) has a metallic helically wound coil (152) and a polymeric coil (154) made up of one or the other of the polymeric materials discussed above. Any other ancillary fibrous materials may be chosen from the remaining group of polymeric materials.

It is within the scope of this invention that each of the polymeric materials can be attached to any allied core member variously by appropriate and safe glues or, if the polymeric materials are thermoplastics, by heating those polymers to cause them to maintain a contact with the core member.

FIG. 6 shows still another variation (160) of the inventive device. The depiction in FIG. 6 is a single turn of a helically wound coil and thus is a partial view cutaway. In this variation, the metallic coil has a coating (164) selected from one group or the other in polymeric materials discussed above. It is within the scope of this invention that the coating be of a single polymeric material, a mixture of the two noted polymeric materials, or a copolymer (block or random) of the two listed materials. The tufts (166) are then fibrous materials chosen from the remaining group of polymeric materials. Metallic coil (162) may be only at least partially coated with the polymeric material or materials (164).

It is also within the scope of this invention that the fibrous members be of a single polymeric material, a mixture of the two noted polymeric materials, or a copolymer (block or random) of the two listed materials.

Not central to the invention but certainly important to the practicality of the device are the ancillary features discussed below. For instance, in FIG. 7, is shown a device made according to this invention (170) which includes through the center lumen of the core member (172), a stretch resisting member (174). Stretch resisting member (174) may be a small diameter wire or more preferably, is a fibrous member running from one end of the vaso-occlusive device to the other. A stretch resistant member is introduced into the device for the purpose of preventing the device from stretching should it need to be relocated or moved or removed from the body due to malplacement or improper choice of size.

FIGS. 8 and 9 show variations on the ways in which the occlusive devices may be delivered. All of the variations discussed above may be variously pushed through a catheter using a pusher wire which is constructed in many ways similar to a guidewire but has certain more inflexible properties allowing it to act as a pusher rather than a leader, as would a guidewire. These inventive devices may also be delivered using the electrolytically severable joints shown in FIG. 8. The variation (180) shown in FIG. 8 encompasses a pusher wire (182) which is electrically conductive and covered by an insulative layer (184). Bare region of metal (186) is designed in such a way that upon application of current to core wire (182), electrolytic joint (186) erodes into the ionic medium surrounding the joint. In most instances, for the use of this device, that ionic medium will be blood. Once the erosion of joint (186) is complete, coil (188) and its attached fibrous polymeric material (shown here as a braid (189)) are left in the selected opening in the human body.

Similarly, FIG. 9 shows a mechanically detachable assembly (190) having a pusher or core wire (192) with joint region (194). Once joint region (194) is removed from the tip of catheter (196), the vaso-occlusive device (198) is free, along with its included braid (199) to remain in the selected site within the human body.

EXAMPLE

We constructed three vaso-occlusive devices for the demonstration of the concept of this invention. The first was a commercially available platinum alloy GDC coil sold by Target Therapeutics of Fremont, Calif. It had no polymeric or fibrous covering of any kind associated with it.

The second coil was a GDC coil, it was covered with a braid constructed of a polypropylene nonabsorbable suture and a polyglycolic acid synthetic absorbable suture. The length and diameter were the same as that of the first controlled GDC coil.

A third prototype was made according to the teachings of this invention. It included a GDC coil listed above covered with a braid constructed of polyethyleneteraphthalate (Dacron) and polyglycolic acid absorbable suture.

Each of the three coils were placed in a canine aneurysm. After 30 days months, the aneurysms were removed and examined.

The occlusion surrounding the control plain platinum coil GDC was sectioned. Multiple sections showed early thrombus without any significant inflammation around the coils. There was only minimal organization of the thrombus and where any organization was seen, it was close to the aneurysm wall.

The aneurysm containing the non-inventive but braided GDC showed more thrombus than the inventive prototype with acute inflammatory cells around the braided coils. The area around the coils showed degenerating acute inflammatory cells, microphages, and fibrin. The central port of the aneurysm was occupied by a blood clot made of fibrin and red cells. Greater healing was observed in the superior and inferior regions of the aneurysm.

The aneurysm containing the inventive coil GDC prototype showed organizing thrombus with microphage around the coils and some giant cell formation. The granulation tissue consisted of smooth muscle cells in a proteoglycan collagenous matrix with focal presence of neocapillaries, chronic inflammation, and fibrin deposits. The two ends of the aneurysm, superior and inferior, showed more healing than the center of the aneurysm. The center of the aneurysm displayed a greater amount of fibrin.

Modifications of the above described variations of carrying out the invention that would be obvious to those of skill in the fields of medical device design generally, and occlusion devices (specifically vaso-occlusion devices), are intended to be within the scope of the following claims.

We claim as our invention:

1. A vaso-occlusive implant with a size, shape, and configuration of such that it may be introduced and implanted into a mammalian blood vessel, the implant comprising in combination an elongated core member, a fibrous member attached to the elongated core member, the elongated core member having a proximal end and a distal end, the fibrous member comprised of a copolymer comprising a first polymeric material, and a second polymeric material different from the first polymeric material.

2. The vaso-occlusive device of claim 1 wherein the elongated core member is metallic.

3. The vaso-occlusive device of claim 2 wherein the metallic elongated core member comprises platinum.

4. The vaso-occlusive device of claim 1 wherein the elongated core member comprises a helical coil member.

5. The vaso-occlusive device of claim 1 wherein the fibrous member is woven into a braid exterior to the elongated core member.

6. The vaso-occlusive device of claim 1 wherein the fibrous member is tufted.

7. The vaso-occlusive device of claim 1 wherein the fibrous member is glued onto said elongated core member.

8. The vaso-occlusive device of claim 1 wherein said elongated core member proximal end comprises a mechanical joint adapted to join to a pusher wire.

9. The vaso-occlusive device of claim 1 wherein said elongated core member proximal end comprises an electrolytically severable joint.

10. The vaso-occlusive device of claim 4 further comprising a stretch-resisting member fixable attached to at least one of said proximal end and distal end.

11. The vaso-occlusive device of claim 1 wherein the elongated core member is comprised of a third polymeric material.

12. The vaso-occlusive device of claim 1 wherein the first polymeric material comprises a non-biodegradable polymeric material.

13. The vaso-occlusive device of claim 1 wherein the first polymeric material is a material selected from the group consisting of polyethyleneterephthalate, polyethylene, polypropylene, Nylon, and polyaramid.

14. The vaso-occlusive device of claim 1 wherein the second polymeric material comprises a biodegradable polymeric material.

15. The vaso-occlusive device of claim 1 wherein the second polymeric material is a material selected from the group consisting of polyglycolic acid, polylactic acid, cotton, and silk.

16. A vaso-occlusive device comprising a core member with a size, shape, and configuration of such that it may be introduced and implanted into a mammalian blood vessel, comprising a core member and a biodegradable fibrous material of a type promoting production of neo-capillaries in said blood vessel.

* * * * *